United States Patent
Feng et al.

(10) Patent No.: US 10,227,547 B2
(45) Date of Patent: Mar. 12, 2019

(54) ASTRAGALUS MEMBRANACEUS SEED RAW OIL, REFINED OIL, PREPARATION METHOD THEREFOR AND USE THEREOF

(71) Applicant: SHANXI ZHENDONG PHARMACEUTICAL CO. LTD., Changzhi County, Shanxi (CN)

(72) Inventors: Qianjin Feng, Taiyuan (CN); Ran Zhou, Taiyuan (CN); Anping Li, Taiyuan (CN); Sufen Liu, Taiyuan (CN); Jin Li, Taiyuan (CN); Cailing Shang, Taiyuan (CN)

(73) Assignee: SHANXI ZHENDONG PHARMACEUTICAL CO., LTD., Shanxi (CN)

( * ) Notice: Subject to any disclaimer, the term of this patent is extended or adjusted under 35 U.S.C. 154(b) by 0 days.

(21) Appl. No.: 14/911,831

(22) PCT Filed: Aug. 15, 2013

(86) PCT No.: PCT/CN2013/081528
§ 371 (c)(1),
(2) Date: Feb. 12, 2016

(87) PCT Pub. No.: WO2015/021631
PCT Pub. Date: Feb. 19, 2015

(65) Prior Publication Data
US 2016/0199429 A1 Jul. 14, 2016

(51) Int. Cl.
| | |
|---|---|
| *A61K 36/481* | (2006.01) |
| *A61K 36/00* | (2006.01) |
| *C11B 3/16* | (2006.01) |
| *A23D 9/00* | (2006.01) |
| *C11B 1/10* | (2006.01) |
| *C11B 3/00* | (2006.01) |
| *C11B 3/06* | (2006.01) |
| *C11B 3/10* | (2006.01) |

(52) U.S. Cl.
CPC ............... *C11B 3/16* (2013.01); *A23D 9/00* (2013.01); *A61K 36/481* (2013.01); *C11B 1/104* (2013.01); *C11B 3/001* (2013.01); *C11B 3/006* (2013.01); *C11B 3/06* (2013.01); *C11B 3/10* (2013.01); *A61K 2236/00* (2013.01); *A61K 2236/37* (2013.01); *Y02P 20/544* (2015.11)

(58) Field of Classification Search
None
See application file for complete search history.

(56) References Cited

U.S. PATENT DOCUMENTS

2009/0258081 A1  10/2009  Minatelli et al.

FOREIGN PATENT DOCUMENTS

| CN | 101317993 A | 12/2008 |
| CN | 101791015 A | 8/2010 |

OTHER PUBLICATIONS

Miraj et al. (2016) Der Pharmacia Lettre 8(6): 59-65.*
International Search Report issued in corresponding application No. PCT/CN2013/081528 dated May 20, 2014 (5 pages).
Penghao Li, et al., "Shayuanzi Zhifangyou Chaolinjie CO2 Cuiqu JI GC-MS Fenxi," (Astragalus complanatus fatty oil obtained by supercritical $CO_2$ extraction technology and the analysis thereof by GC-MS), Zhongyaocai, No. 09, vol. 26 (Sep. 30, 2003), pp. 640 and 641.

* cited by examiner

*Primary Examiner* — Christopher R Tate
*Assistant Examiner* — Russell G Fiebig
(74) *Attorney, Agent, or Firm* — Birch, Stewart, Kolasch & Birch, LLP (57) ABSTRACT

The invention belongs to the field of traditional Chinese medicine (TCM), and in particular relates to an *astragalus membranaceus* seed raw oil and refined oil extracted from *astragalus membranaceus* seeds by using a supercritical extraction method, and to a use thereof in the preparation of health-care products. The *astragalus membranaceus* seed raw oil is obtained by supercritical $CO_2$ fluid extraction on the *astragalus membranaceus* seeds; and the *astragalus membranaceus* seed refined oil is obtained by physically refining the *astragalus membranaceus* seed raw oil. The *astragalus membranaceus* seed raw oil and refined oil have the effects of preventing thrombosis and dilating blood vessels, can also prevent diseases such as atherosclerosis, hypertension, hyperglycemia and high cholesterol, and can be used as a long-term dietary health-care oil product for cardiovascular patients.

2 Claims, 1 Drawing Sheet

ASTRAGALUS MEMBRANACEUS SEED RAW OIL, REFINED OIL, PREPARATION METHOD THEREFOR AND USE THEREOF

FIELD OF THE INVENTION

The present invention belongs to the field of traditional Chinese medicine (TCM), and in particular relates to an *Astragalus membranaceus* seed raw oil and refined oil extracted from *Astragalus membranaceus* seeds by using a supercritical extraction method, preparation methods thereof, and use thereof in the preparation of health-care products and drugs.

BACKGROUND OF THE INVENTION

*Astragalus membranaceus*, known as "huang qi" in Chinese, is a collective name of plant and Chinese medicinal material. The plant of *Astragalus membranaceus* mainly grows in Inner Mongolia, Shanxi, Gansu, and Heilongjiang provinces of China, etc., and has been listed in the national third-class protected plant category in China. As Chinese medicinal material, *Astragalus membranaceus* is the root portion of *Astragalus membranaceus* (Fisch.) Bge. or *Astragalus membranaceus* var. Mongholicus (Bge.) Hsiao of the herbaceous Fabaceae family, belonging to the famous bulk medicinal materials in China. In ancient China, *Astragalus membranaceus* was termed "Sacred medicine with the effects of tonifying Qi and consolidating exterior". So far *Astragalus membranaceus* has been used as a herbal medicine for more than two thousand years, having the effects of tonifying Qi and consolidating exterior, inducing diuresis to alleviate edema, expelling toxins and draining pus, promoting granulation, improving the body immunologic function, protecting liver, increasing secretion of urine, anti-aging, anti-stress, lowering blood pressure, and relatively broad-spectrum antibiosis.

*Astragalus membranaceus*, being sweet in taste and slightly warm in property, acts on the channels of liver, spleen, lung and kidney. Its major pharmaceutical effects include benefiting Qi and consolidating exterior, arresting sweating for relieving desertion, expelling pus of sores and promoting granulation, and inducing diuresis to remove edema. Based on the five-elements theory of traditional Chinese medicine, spring corresponds to the liver, as a result, nourishing the liver-Qi is crucial to the health preservation in spring. As an excellent tonic, *Astragalus membranaceus* plays a certain role of tonifying Qi in the spring season of growth and development. The gruel or soup cooked with *Astragalus membranaceus* has the pharmaceutical effects of benefiting blood and tonifying Qi.

*Astragalus membranaceus* has been artificially cultivated in China since the early 1970s, especially after the 1980s, the cultivation amount of it in China has been increasing year by year. However, up to now research on the cultivated *Astragalus membranaceus* has absolutely focused on the root portion that is used as Chinese medicinal material, and the research on other parts of *Astragalus membranaceus*, especially other relevant parts of production chain, has remained almost a blank. The current research situation will limit the comprehensive utilization of the plant *Astragalus membranaceus* to some extent, especially the development of industrial chain of *Astragalus membranaceus* cultivation. Accordingly, how to better exploit other products with beneficial value in the industrial chain of *Astragalus membranaceus* has become a core topic of *Astragalus membranaceus* and even in the field of Chinese medicinal material, which has received full attention, leading to extensive research.

Oil is considered to be the highest calorie nutrient substance in the human diet, and the oil content needs to be ensured in the process of human dietary intake. However, with the socioeconomic development and the continuous improvement of people's living standard, oil and oilseed resources' contradictions in short supply have become increasingly prominent within the country. In the meantime, people now pay more attention to nutritional and health care functions of cooking oil. As a result, active development of new cooking oil resources is of great significance, especially for nutritional and health care cooking oil with special effects on human health, with special components of fatty acids, or containing special physiologically active substances.

SUMMARY OF THE INVENTION

The present invention provides an *Astragalus membranaceus* seed raw oil obtained from *Astragalus membranaceus* seeds by a supercritical extraction method and a preparation method thereof, an *Astragalus membranaceus* seed refined oil obtained from the raw oil by a refinement process and a preparation method thereof, and also a new use of the raw oil and refined oil in the preparation of health-care products for the prevention of diseases and drugs.

The above-mentioned issues can be realized by the following technical solutions.

The present invention provides an *Astragalus membranaceus* seed raw oil, obtained by extracting the *Astragalus membranaceus* seeds with a supercritical $CO_2$ fluid.

In some examples of the invention, the extracting is carried out at a $CO_2$ flow rate adjusted to maximum, under a constant temperature of 30-50° C. and a constant pressure of 250-350 Pa, and lasts for 1.5-2.5 hours.

In some examples, the *Astragalus membranaceus* seed raw oil is made into clinically acceptable dosage forms, including tablets, dripping pills, capsules, granules, mixtures and pills, by conventional technologies after being added with conventional excipients.

The present invention further provides an *Astragalus membranaceus* seed refined oil, obtained by physically refining the *Astragalus membranaceus* seed raw oil, wherein the refining comprises:

(a) a degumming step: wherein the *Astragalus membranaceus* seed raw oil was heated to 45-55° C., then hot water, in a weight percentage of 3-5% with respect to the weight of the raw oil and having a temperature similar to that of the raw oil, was added and mixed well with the raw oil to form a first mixture, and the first mixture was heated to 75-85° C. under stirring, followed by standing and layering at 75-85° C., then a lower layer of water and gum was removed, and an upper layer of degummed oil was obtained;

(b) a deacidification step: wherein the degummed oil was collected and heated to 50-70° C. under shaking, then NaOH aqueous solution in a concentration of 7-12% by weight was added into the degummed oil at 50-70° C. to form a second mixture, the second mixture is centrifuged and an upper layer of oil was collected and heated to 70-90° C., then the oil was washed with hot water and was centrifuged, obtaining a deacidified oil in an upper layer; and (c) a decoloration step: wherein the deacidified oil was collected and heated to 70-90° C., then an active white clay in a weight percentage of 4-6% with respect to the weight of the deacidified oil was added into the deacidified oil for performing decoloration at 70-90° C. for at least once, after which the deacidified oil was centrifuged, obtaining a refined oil in an upper layer.

In one preferred example, the *Astragalus membranaceus* seed refined oil is prepared by the following steps:

(a) a degumming step: wherein the *Astragalus membranaceus* seed raw oil was heated to 50° C., then hot water, in a weight percentage of 4% with respect to the weight of the raw oil and having a temperature similar to that of the raw oil, was added and mixed well with the raw oil to form a first mixture, and the first mixture was heated to 80° C. under stirring, followed by standing and layering for 6 hours at 80° C., then a lower layer of water and gum was removed, and an upper layer of degummed oil was obtained;

(b) a deacidification step: wherein the degummed oil was collected and heated to 60° C. under shaking, then NaOH aqueous solution in a concentration of 10% by weight was added into the degummed oil at 60° C. to form a second mixture, the second mixture is centrifuged and an upper layer of oil was collected and heated to 80° C., then the oil was washed with hot water and was centrifuged, obtaining a deacidified oil in an upper layer; and (c) a decoloration step: wherein the deacidified oil was collected and heated to 80° C., then an active white clay in a weight percentage of 5% with respect to the weight of the deacidified oil was added into the deacidified oil for performing decoloration at 80° C. for twice, after which the deacidified oil was centrifuged, obtaining a refined oil in an upper layer.

In a further example, the decoloration step (c) is followed by (d) a deodorization step: wherein the refined oil was collected and heated to 70-90° C., then stream was introduced through a glass tube and flowed upwards to perform stripping such that uniform mass transfer occurs between the oil and the stream to produce a deodorized oil, thereafter the deodorized oil is dehydrated to produce a new refined oil.

In a most preferred example, in the deodorization step, the refined oil obtained in the step (c) was collected and heated to 80° C., then stream was introduced through a glass tube and flowed upwards to perform stripping such that uniform mass transfer occurs between the oil and the stream to produce a deodorized oil, thereafter the deodorized oil is dehydrated to produce a new refined oil.

In some examples, the *Astragalus membranaceus* seed refined oil is prepared into clinically acceptable dosage forms, including tablets, dripping pills, capsules, granules, mixtures and pills, by the conventional technologies after being added with conventional excipients.

The present invention further provides a method for the preparation of the *Astragalus membranaceus* seed raw oil, comprising an extracting step, wherein the *Astragalus membranaceus* seeds were extracted with a supercritical $CO_2$ fluid for 1.5-2.5 hours at a constant temperature of 30-50° C. under a constant pressure of 250-350 Pa.

The present invention further provides a method for the preparation of the *Astragalus membranaceus* seed refined oil, comprising the extracting step for the preparation of the *Astragalus membranaceus* seed raw oil, wherein the extracting step is followed by (a) a degumming step: wherein the *Astragalus membranaceus* seed raw oil was heated to 45-55° C., then hot water, in a weight percentage of 3-5% with respect to the weight of the raw oil and having a temperature similar to that of the raw oil, was added and mixed well with the raw oil to form a first mixture, and the first mixture was heated to 75-85° C. under stirring, followed by standing and layering at 75-85° C., then a lower layer of water and gum was removed, and an upper layer of degummed oil was obtained;

(b) a deacidification step: wherein the degummed oil was collected and heated to 50-70° C. under shaking, then NaOH aqueous solution in a concentration of 7-12% by weight was added into the degummed oil at 50-70° C. to form a second mixture, the second mixture is centrifuged and an upper layer of oil was collected and heated to 70-90° C., then the oil was washed with hot water and was centrifuged, obtaining a deacidified oil in an upper layer; and (c) a decoloration step: wherein the deacidified oil was collected and heated to 70-90° C., then an active white clay in a weight percentage of 4-6% with respect to the weight of the deacidified oil was added into the deacidified oil for performing decoloration at 70-90° C. for at least once, after which the deacidified oil was centrifuged, obtaining a refined oil in an upper layer.

In a preferred example for the preparation of the *Astragalus membranaceus* seed refined oil, the extracting step is followed by (a) a degumming step: wherein the *Astragalus membranaceus* seed raw oil was heated to 50° C., then hot water, in a weight percentage of 4% with respect to the weight of the raw oil and having a temperature similar to that of the raw oil, was added and mixed well with the raw oil to form a first mixture, and the first mixture was heated to 80° C. under stirring, followed by standing and layering for 6 hours at 80° C., then a lower layer of water and gum was removed, and an upper layer of degummed oil was obtained;

(b) a deacidification step: wherein the degummed oil was collected and heated to 60° C. under shaking, then NaOH aqueous solution in a concentration of 10% by weight was added into the degummed oil at 60° C. to form a second mixture, the second mixture is centrifuged and an upper layer of oil was collected and heated to 80° C., then the oil was washed with hot water and was centrifuged, obtaining a deacidified oil in an upper layer; and (c) a decoloration step: wherein the deacidified oil was collected and heated to 80° C., then an active white clay in a weight percentage of 5% with respect to the weight of the deacidified oil was added into the deacidified oil for performing decoloration at 80° C. for twice, after which the deacidified oil was centrifuged, obtaining a refined oil in an upper layer.

In a further example for the preparation of the *Astragalus membranaceus* seed refined oil, the decoloration step (c) is followed by (d) a deodorization step: wherein the refined oil was collected and heated to 70-90° C., then stream was introduced through a glass tube and flowed upwards to perform stripping such that uniform mass transfer occurs between the oil and the stream to produce a deodorized oil, thereafter the deodorized oil is dehydrated to produce a new refined oil.

In a most preferred example for the preparation of the *Astragalus membranaceus* seed refined oil, in the deodorization step, the refined oil obtained in the step (c) was collected and heated to 80° C., then stream was introduced through a glass tube and flowed upwards to perform stripping such that uniform mass transfer occurs between the oil and the stream to produce a deodorized oil, thereafter the deodorized oil is dehydrated to produce a new refined oil.

The present invention further provides a use of the *Astragalus membranaceus* seed raw oil in the preparation of health-care products and drugs with functions of lowering blood glucose, hyperlipoidemia, triglyceride, and cholesterol.

The present invention further provides a use of the *Astragalus membranaceus* seed refined oil in the preparation of health-care products and drugs with functions of lowering blood glucose, hyperlipoidemia, triglyceride, and cholesterol.

The present invention further provides a use of the *Astragalus membranaceus* seed refined oil in the preparation of edible blend oil.

The present invention further provides an edible blend oil, which is prepared by proportionally blending the *Astragalus membranaceus* seed refined oil with conventional sesame oil, olive oil, grape seed oil, walnut oil, soybean oil, sunflower seed oil, or peanut oil.

The term *Astragalus membranaceus* seed as described above and below in the present invention, refers to the seed now available for cultivation of the plant *Astragalus membranaceus*, and there is no difference in nutrient substances and effects between seeds obtained from different growth regions or by different cultivation methods.

In some examples, the *Astragalus membranaceus* seed is treated by steps such as impurity elimination, washing clean and air drying in prior to use. Alternatively, the *Astragalus membranaceus* seed is dried in an oven at 105° C. for 2 hours, then pulverized and ground to 40 meshes in prior to use.

The goal of the invention is to investigate and develop the *Astragalus membranaceus* seed resource, and to provide a process route for preparing an *Astragalus membranaceus* seed oil by extracting the *Astragalus membranaceus* seed with a supercritical $CO_2$ fluid. The fatty acid composition thereof is analyzed and identified by GC-MS, and the contents of various vitamins and micro elements in the *Astragalus membranaceus* seed oil are simultaneously analyzed and determined.

The analysis results demonstrates that the *Astragalus membranaceus* seed oil is firstly found rich in nutrient components, having extremely high nutrition utilization value for human. It contains relatively high content of Vitamin E and various fatty acid components, such as tetradecanoic acid, palmitic acid, octadecanoic acid, arachic acid, behenic acid, oleic acid, linoleic acid and linolenic acid, wherein the linoleic acid and linolenic acid are polyunsaturated fatty acids, and the content of linoleic acid and linolenic acid is 44.5% and 22.8% by weight respectively (i.e. the weight ratio of linoleic acid to linolenic acid is 2:1), showing that the *Astragalus membranaceus* seed oil is a functional oil with nutrition and health care value.

In the present invention, an *Astragalus membranaceus* seed oil is extracted out by a supercritical $CO_2$ extraction method which is an efficient green extraction technology, and then the *Astragalus membranaceus* seed oil is refined to produce a refined oil. Therefore, the present invention provides necessary technical parameters for the development of *Astragalus membranaceus* seed oil industry.

The *Astragalus membranaceus* seed refined oil can not only be made into health-care products and drugs for daily maintenance, but also be blended with daily sesame oil, olive oil, grape seed oil, walnut oil, soybean oil, sunflower seed oil, or peanut oil in accordance with a certain proportion such that the ratio of ω-6 to ω-3 in the blend oil is adjusted to 2-4:1, which is in accordance with the recommended standards adopted by The International Scientific Committee on Food. The blend oil therefore can be used as an oil product for daily cooking, cold vegetable dish in sauce, health-care and dining.

Experiment 1

1. Physical and Chemical Property Determination of *Astragalus membranaceus* Seed Refined Oil The *Astragalus membranaceus* seed raw oil and refined oil obtained in example 1 described below are tested to determine the physical and chemical property parameters, and the results are shown in Table 1:

TABLE 1

Physical and chemical property comparison between *Astragalus membranaceus* seed crude oil and refined oil

| Physical and chemical indexes | Crude oil | Refined oil |
| --- | --- | --- |
| Transparency, odour and taste | Brown | Pale yellow and transparent |
| Peroxide value | 0.11 g/100 g | 0.14 g/100 g |
| Acid value | 4.8 mg/g | 0.8 g/mg |
| Iodine value | 148 g/100 g | 137.5 g/mg |
| Saponification value | 185 mg/g | 182.9 mg/g |
| Phospholipids | 0.46 g/100 g | |

The data in Table 1 shows that, each property parameter of the *Astragalus membranaceus* seed refined oil has achieved a satisfactory level. The refined oil product is transparent with light color and improved quality that is beneficial to oil storage. The refined oil product meets the standard of edible vegetable oil.

2. GC-MS Test and Analysis of Fatty Acids in *Astragalus membranaceus* Seed Oil

Figure 1:
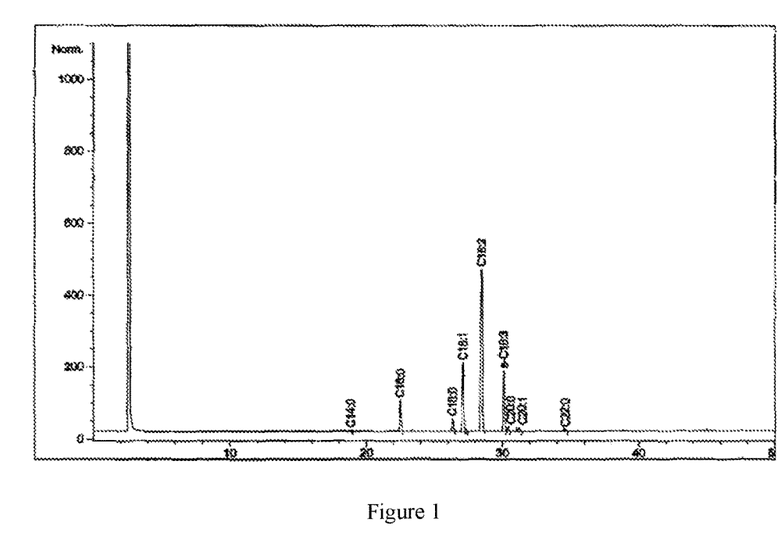
FIG. 1 shows the GC-MS spectrum of the *Astragalus membranaceus* seed refined oil obtained in example 1.
Figure 2:
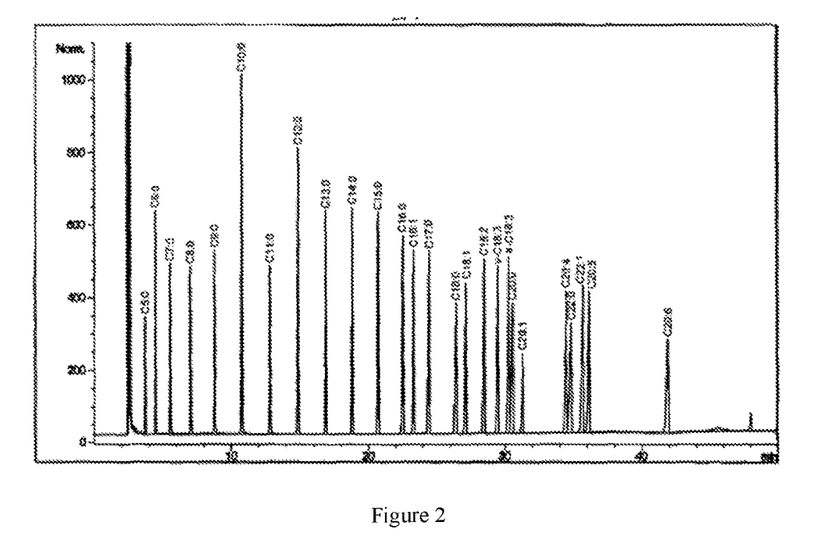
FIG. 2 shows the GC-MS spectrum of fatty acids standards.

*Astragalus membranaceus* seed oil sample was tested by hydrolysis extraction-gas chromatography method that is used for determination of total fat, saturated fat and unsaturated fat in food products according to GB/T 22223-2008. FIG. 1 shows the test results. FIG. 2 shows a fatty acid standard spectrum that is used as a reference to identify the components contained in the *Astragalus membranaceus* seed raw oil and refined oil, and to calculate the content of the components before and after refinement. The results are shown in Table 2.

TABLE 2

Fatty acid components of *Astragalus membranaceus* seed oil

| Name | Contents in crude oil (%) | Contents in refined oil (%) |
| --- | --- | --- |
| Tetradecanoic (C14:0) acid | 0.3 | 0.17 |
| Palmitic acid (C16:0) | 6.7 | 5.95 |
| Zoomaric acid (C16:1n7) | | 0.09 |
| Octadecanoic (C18:0) acid | 3.0 | 2.71 |
| Oleic acid (C18:1n9c) | 17.8 | 16.73 |
| Linoleic acid (C18:2n6c) | 44.5 | 51.72 |
| α-Linolenic (C18:3n3) acid | 22.8 | 15.25 |
| Arachic acid (C20:0) | 1.1 | 0.95 |
| cis-11-Eicosenoic (C20:1) acid | 0.4 | 0.85 |
| Behenic acid (C22:0) | 0.3 | 0.33 |
| Omega-3 fatty acids | 22.8 | 15.25 |
| Omega-6 fatty acids | 44.5 | 51.72 |
| Omega-9 fatty acids | 17.8 | 16.73 |
| Saturated fatty acids | 11.3 | 10.11 |
| Monounsaturated fatty acids | 18.3 | 17.67 |
| Polyunsaturated fatty acids | 67.3 | 66.97 |
| Content ratio of saturated fatty acids to unsaturated fatty acids | 13 | 12 |

3. Determination of Nutrition Components in *Astragalus membranaceus* Seed Oil

The nutrition components in *Astragalus membranaceus* seed raw oil and refined oil were detected based on the methods specified in GB5413.9-2010, GB5009.93-2010, GB/T5009.14-2003, GB/T5009.90-2003, GB/T5009.92-2003, GB/T5009.12-2003, and GB/T22220-2008, and the results are shown in table 3.

TABLE 3

Determination results in *Astragalus* membranaceus seed oil

| Detection items | Detection results in crude oil | Detection results in refined oil |
|---|---|---|
| Total amount of Vitamin E mg/100 g | 55.5 | 89.6 |
| α-Tocopherol mg/100 g | 54.2 | 83.2 |
| γ + β-Tocopherol mg/100 g | 1.30 | 6.45 |
| Cholesterol mg/100 g | Not detected | Not detected |
| Fe mg/100 g | 4.89 | 0.35 |
| Calcium mg/100 g | 6.53 | 0.13 |
| Zinc mg/100 g | 0.47 | 0.15 |

According to the above data in table 3, the *Astragalus membranaceus* seed raw oil comprises fatty acids in a total amount of 96.9% by weight, monounsaturated fatty acids in an amount of 18.3% by weight, and polyunsaturated fatty acids in an amount of 67.3%, wherein the unsaturated fatty acids constitutes 88% of the total fatty acids by weight; while the *Astragalus membranaceus* seed refined oil comprises fatty acids in a total amount of 94.75% by weight, monounsaturated fatty acid in an amount of 17.67% by weight, and polyunsaturated fatty acids in an amount of 66.97% by weight, wherein and the unsaturated fatty acids constitutes 89% of the total fatty acids by weight, and moreover, the *Astragalus membranaceus* seed refined oil comprises Vitamin E and Calcium in a high amount but does not comprise cholesterol. The analysis results fully shows that *Astragalus membranaceus* seed oil is a high quality raw material in the preparation of health-care oil for preventing cardiovascular diseases, and that the *Astragalus membranaceus* seed oil has the efficacy of nutrient health-care and preventing diseases as a functional oil rich in unsaturated fatty acids. The *Astragalus membranaceus* seed oil has the effects of preventing thrombosis and dilating blood vessels, and has the capabilities in the prevention of diseases such as atherosclerosis, hypertension, hyperglycemia and high cholesterol, thus can be used as health-care oil products for patients with cardiovascular diseases in the long-term dietary therapy.

To sum up, the *Astragalus membranaceus* seed oil in the invention, whether raw oil or refined oil obtained after refinement, is rich in nutrient components, and has very high nutrient health-care and food therapy value, thus will have broader prospects of development. Moreover, it has opened up a new resource and use for the *Astragalus membranaceus* industry of Chinese medicine, and further improved the life quality of human beings.

Experiment 2

1 Materials and Methods
1.1 Experimental Oil

The *Astragalus membranaceus* seed refined oil was self-made in our study group, the *Astragalus membranaceus* seed refined oil obtained in example 1 described below was employed to conduct the experiment, comprising linoleic acid, linolenic acid, oleic acid and unsaturated fatty acids; arachis oil sold in the market was used as a control.
1.2 Experimental Animals and Feed A total number of 60 healthy male SD rats were used in this study and randomly assigned to 6 treatment groups with 10 rats per group. The rats were 6-8 weeks old with body weight in range of 160-190 g, purchased from Laboratory Animal Center, Academy of Military Medical Sciences with the License number SCXK-(Army) 2007-004.

SPF-grade chow diet for rat and mouse was provided by Beijing Keaoxieli Feed Co., Ltd., Manufacture with License Number: SCXK (Beijing) 2009-0012. The drinking water was obtained from tap water by High Pressure Sterilization. The animals had free access to rat chow and tap water ad libitum.
1.3 Experimental Apparatuses Model SELECTRA-E Automatic biochemical analyzer, Vital Scientific, The Netherlands; Model HEMAVET 950 Automatic five classification animal blood analyzer, Drew Scientific Limited, UK; Low speed large capacity centrifuge, etc. Total cholesterol detection kit, triglyceride kit, and high density lipoprotein cholesterol kit were provided by Beijing Zhongsheng High-tech Bioengineering Company.
1.4 Dose Selection and Experimental Methods The study used intragastric administration. The rats were divided into three dose groups of the *Astragalus membranaceus* seed oil, i.e. High-dose, Middle-dose and Low-dose groups. In addition, there are also a normal control group, a model group, and an arachis oil control group. In terms of the specific doses, the normal control group and model group were given distilled water with a dose of 5 g/kg, the arachis oil control group at a dose of 5 g/kg, and High-dose, Middle-dose and Low-dose groups were given *Astragalus membranaceus* seed oil at doses of 5 g/kg, 3 g/kg, and 1 g/kg, respectively.

After the rats were fed with fundamental feed for 7 days, they were subjected to overnight fasting and weighed before blood sampling from the tail. The serum TC, TG, and high density lipoprotein cholesterol (HDL-C) were detected. Based on body weight, the rats were randomly divided into 6 groups, with each group containing 10 rats. The normal control group was fed with conventional feed, the other groups (three dose groups, model group and positive control group) were fed with high fat feed. One time a day, seven days a week, and the total administration period was five weeks.

The animals were observed everyday, body weight and food intake were measured once a week. After consecutive administration for 2 weeks, the blood glucose value was detected per week by tail vein sampling; at the end of the experiment, the animals were fasted for 12-16 hours, then anaesthetized by intraperitoneal injection of pentobarbital sodium (50 mg/kg), the blood was drawn from abdominal aorta using negative pressure tubes to detect the biochemical indexes.
1.5 Data Analysis Using SPSS 17.0 software to calculate the mean and standard deviation of measurement data among all groups, then conduct t-test, a probability value of <0.05 was considered significant.
2 Experimental Results
2.1 The Toxicity of *Astragalus membranaceus* Seed Oil and Effects on Rat Body Weight According to the procedures of toxicity test, a total number of 40 ICR mice (SPF-grade) were used in this study, 4-5 weeks old, body weight range 14-17 g, male and female in half, purchased from Laboratory Animal Center, Academy of Military Medical Sciences with the License number SCXK-(Army) 2007-004. Following single dose intragastric administration of the vegetable oil from Chinese herbal medicine, the mice were observed for two weeks. No toxicity reaction or death condition was found during the experiment, so the *Astragalus membranaceus* seed oil was considered nontoxic.

Effects of *Astragalus membranaceus* seed oil on rat body weight is shown in Table 1.

TABLE 1

Effects of *Astragalus membranaceus* seed oil on rat body weight

| | 1 W | 2 W | 3 W | 4 W | 5 W | 6 W |
|---|---|---|---|---|---|---|
| Water control | 237.100 ± 13.63 | 300.000 ± 13.67 | 358.600 ± 17.58 | 402.400 ± 21.71 | 433.500 ± 25.09 | 456.000 ± 31.23 |
| Oil control | 235.800 ± 15.70 | 245.000 ± 28.13** | 272.900 ± 20.17** | 263.800 ± 21.84** | 257.600 ± 21.38** | 257.200 ± 20.35** |
| Model group | 238.600 ± 12.14 | 241.100 ± 11.10** | 263.500 ± 12.08** | 250.600 ± 12.92** | 246.000 ± 14.87** | 242.200 ± 14.16** |
| Low-dose | 235.000 ± 9.10 | 238.000 ± 12.92** | 254.700 ± 12.86** | 246.500 ± 14.41** | 241.600 ± 16.52** | 241.900 ± 16.20** |
| Middle-dose | 232.000 ± 10.96 | 231.400 ± 13.44** | 254.900 ± 11.17** | 251.900 ± 12.77** | 248.700 ± 13.15** | 244.700 ± 13.679** |
| High-dose | 237.100 ± 13.63 | 235.700 ± 12.85** | 256.100 ± 24.63** | 247.200 ± 19.91** | 242.900 ± 20.11** | 244.500 ± 18.81** |

Note:
compared with the normal control group, * $p < 0.05$, ** $p < 0.01$;
compared with the AA model group, ▲$p < 0.05$, ▲▲$p < 0.01$;
compared with the oil control group, ●$p < 0.05$, ●●$p < 0.01$.

During the course of administration, in Week 1, compared with the normal control group, the body weight in the three groups of *Astragalus membranaceus* seed oil and oil control group exhibited no significant difference. From Week 2 to Week 6, the body weight in the other groups decreased significantly compared with that in the normal control group, even to extremely significant difference ($p<0.01$), the major reason is that the high fat feed is of poor palatability, leading to reduced amount of food intake, and in turn significantly reduced body weight, which has nothing to do with the *Astragalus membranaceus* seed oil. Compared with the oil control group, the body weight in the three groups of *Astragalus membranaceus* seed oil exhibited a decreasing trend, but the difference failed to achieve statistical significance ($p>0.05$). Compared with the model group, the body weight in the three groups of *Astragalus membranaceus* seed oil exhibited no significant difference ($p>0.05$).

2.2 Effects of *Astragalus membranaceus* Seed Oil on Blood Glucose as Shown in Table 2

TABLE 2

Effects of *Astragalus membranaceus* seed oil on blood glucose

| | Day 20 | Day 24 | Day 27 | Day 31 |
|---|---|---|---|---|
| Water control | 6.630 ± 0.66 | 6.500 ± 0.56 | 6.370 ± 0.56 | 6.670 ± 0.54 |
| Oil control | 6.490 ± 0.61 | 6.310 ± 0.63 | 6.440 ± 0.71 | 6.480 ± 0.62 |
| Model group | 6.440 ± 0.65 | 6.180 ± 0.51 | 6.200 ± 0.54 | 6.280 ± 0.53 |
| Low-dose | 5.890 ± 0.48*▲ | 5.990 ± 0.66 | 6.050 ± 0.86 | 6.030 ± 0.86 |
| Middle-dose | 6.330 ± 0.48 | 6.280 ± 0.71 | 6.230 ± 0.83 | 5.430 ± 0.65**▲● |
| High-dose | 6.090 ± 0.33* | 5.980 ± 0.64 | 6.190 ± 0.49 | 5.570 ± 0.76** |

Note:
compared with the normal control group, *$p < 0.05$, **$p < 0.01$;
compared with the AA model group, ▲$p < 0.05$, ▲▲$p < 0.05$;
compared with the oil control group, •$p < 0.05$, •• $p < 0.01$.

On Day 20, Day 24, Day 27, and Day 31 after administration, blood glucose was detected by tail vein sampling among the three groups of *Astragalus membranaceus* seed oil, arachis oil control group, the model control group and normal control group. Compared with the normal control, oil control and model control group, the blood glucose in groups of *Astragalus membranaceus* seed oil exhibited a decreasing trend, of which, on Day 20 and Day 31, the blood glucose in High-dose group exhibited a significant difference compared with that in normal group ($p<0.05$, $p<0.01$); on Day 31, the blood glucose in High-dose group exhibited a significant difference compared with that in model group ($p<0.05$); on Day 31, the blood glucose in Middle-dose group exhibited a extremely significant difference compared with that in normal group, model group and oil control group ($p<0.01$); compared with normal group and model group, the blood glucose in Low-dose group exhibited a decreasing trend, and only exhibited a significant difference on Day 20 ($p<0.05$); on the other time points the difference failed to achieve statistical significance ($p>0.05$).

2.3 Effects of *Astragalus membranaceus* Seed Oil on the Level in Total Triglyceride of Rats Effects of *Astragalus membranaceus* seed oil on the level in total triglyceride of rats is shown in Table 3.

TABLE 3

Effects of *Astragalus membranaceus* seed oil on the level in total triglyceride of rats

| | TG (triglyceride) | |
|---|---|---|
| Group | Before experiment | After experiment |
| Water control | 0.98 ± 0.42 | 1.01 ± 0.58▲▲ |
| Oil control | 0.99 ± 0.39 | 1.58 ± 0.56 |

TABLE 3-continued

Effects of *Astragalus membranaceus* seed oil on the level in total triglyceride of rats

| | TG (triglyceride) | |
|---|---|---|
| Group | Before experiment | After experiment |
| Model group | 1.03 ± 0.40 | 1.76 ± 0.49 |
| Low-dose | 0.97 ± 0.42 | 1.45 ± 0.52 |

TABLE 3-continued

Effects of *Astragalus* membranaceus seed oil on the level in total triglyceride of rats

| Group | TG (triglyceride) | |
|---|---|---|
| | Before experiment | After experiment |
| Middle-dose | 0.99 ± 0.41 | 1.27 ± 0.46▲● |
| High-dose | 1.02 ± 0.40 | 1.21 ± 0.43▲● |

Note:
compared with the normal control group, * $p < 0.05$, ** $p < 0.01$;
compared with the AA model group, ▲$p < 0.05$, ▲▲$p < 0.01$;
compared with the oil control group, ●$p < 0.05$, ●●$p < 0.01$.

As shown from the results, after administration of *Astragalus membranaceus* seed oil for 31 days, there was a significant difference between control group and model group, indicating successful establishment of the model. After administration of *Astragalus membranaceus* seed oil for 31 days, the serum TG content in High-dose and Middle-dose groups decreased significantly, and exhibited a significant difference compared with that in oil control group and model group ($p<0.05$).

2.4 Effects of *Astragalus membranaceus* Seed Oil on the Level in Total Cholesterol of Rats Effects of *Astragalus membranaceus* seed oil on the level in total cholesterol of rats is shown in Table 4.

TABLE 4

Effects of *Astragalus* membranaceus seed oil on the level in total cholesterol of rats

| Group | Serum total cholesterol | |
|---|---|---|
| | Before experiment | After experiment |
| Water control | 2.53 ± 0.38 | 2.54 ± 0.22▲▲ |
| Oil control | 2.49 ± 0.50 | 3.51 ± 0.40 |
| Model group | 2.53 ± 0.50 | 3.68 ± 0.38 |
| Low-dose | 2.52 ± 0.46 | 3.52 ± 0.35 |
| Middle-dose | 2.47 ± 0.45 | 2.89 ± 0.41▲ |
| High-dose | 2.43 ± 0.43 | 2.85 ± 0.32▲● |

Note:
compared with the normal control group, * $p < 0.05$, ** $p < 0.01$;
compared with the AA model group, ▲$p < 0.05$, ▲▲$p < 0.01$;
compared with the oil control group, ●$p < 0.05$, ●●$p < 0.01$.

As shown from the results, after administration of *Astragalus membranaceus* seed oil for 31 days, there was a significant difference between control group and model group, indicating successful establishment of the model, but there was no significant difference between oil control group and model group. The content of total cholesterol in High-dose group of *Astragalus membranaceus* seed oil decreased significantly, and exhibited a significant difference compared with that in oil control group and model group ($p<0.05$). The content of total cholesterol in Middle-dose group of *Astragalus membranaceus* seed oil decreased significantly, and exhibited a significant difference compared with that in model group ($p<0.05$).

2.5 Effects of *Astragalus membranaceus* Seed Oil on the Level in High Density Lipoprotein Cholesterol (HDL-C) of Rats Effects of *Astragalus membranaceus* seed oil on HDL-C of rats is shown in Table 5.

TABLE 5

Effects of *Astragalus* membranaceus seed oil on the level in HDL-C of rats

| Group | HDL-C | |
|---|---|---|
| | Before experiment | After experiment |
| Water control | 0.98 ± 0.42 | 0.99 ± 0.58 |
| Oil control | 0.95 ± 0.39 | 0.88 ± 0.56 |
| Model group | 1.00 ± 0.37 | 0.77 ± 0.52 |
| Low-dose | 0.99 ± 0.42 | 0.89 ± 0.52 |
| Middle-dose | 1.02 ± 0.41 | 0.95 ± 0.46▲● |
| High-dose | 0.99 ± 0.40 | 1.02 ± 0.43▲● |

Note:
compared with the normal control group, * $p < 0.05$, ** $p < 0.01$;
compared with the AA model group, ▲$p < 0.05$, ▲▲$p < 0.05$;
compared with the oil control group, ●$p < 0.05$, ●●$p < 0.01$.

As shown from the results, after administration of *Astragalus membranaceus* seed oil for 31 days, there was a significant difference compared with oil control group and model group. The content of HDL-C in Middle-dose and High-dose groups of *Astragalus membranaceus* seed oil increased significantly, and exhibited a significant difference compared with that in oil control group and model group ($p<0.05$).

3 Discussion

It is proven from the experimental research that administration of High-dose and Middle-dose *Astragalus membranaceus* seed oil can significantly decrease the levels in blood glucose, serum TC, and TG of rats, and with the increase of dose, the content of HDL-C exhibits an increasing trend.

Committee for Human Nutritional Oils, Scientific Committee on Food of EEC, British Committee on Nutrition Foundation and The Science Council of Canada recommend that the intake ratio of linoleic acid to α-linolenic acid should be 4:1, and that a higher ratio of ω-6/ω-3 is not beneficial to preventing cardiovascular diseases (CVD). Compared to the single cooking oil, *Astragalus membranaceus* seed oil has higher content of α-linolenic acid, and the intake ratio of ω-6 to ω-3 is in accordance with the recommended standards.

The experimental results fully showed that *Astragalus membranaceus* seed oil has functions and health-care effects of lowering blood glucose and blood lipid, and preventing cardiovascular and cerebrovascular diseases, so is considered to be a healthy oil product rich in nutritional components.

BRIEF DESCRIPTION OF THE DRAWINGS

In order to make the invention description easy to be understood clearly, the invention is further illustrated in detail based on specific examples in the invention in combination with drawings, wherein.

DETAILED DESCRIPTION OF THE EXAMPLES

The *Astragalus membranaceus* seed raw materials used in each of the following examples in the invention are provided by Marketing Cooperative of Ying County in Shanxi province, and a retention sample is stored in the scientific experiment center of Shanxi College of Traditional Chinese Medicine, which is just used as a typical example to illustrate the technical effect of the proposal in the invention. Other reagents, for example $CO_2$ in food grade with a purity of 99.5%, active white clay, active carbon, silicone, diatomaceous earth, anhydrous ethanol, petroleum ether and NaOH, are all purchased from the market.

The involved apparatuses include: supercritical fluid extraction system (Thar Technologies Inc., USA), Model KDC-1044 low speed centrifuge, Model THZ-D air bath constant temperature oscillator, Model SHA-C constant temperature oscillator, Magnetic Heating Stirrer, electronic balance, and Model cary50 UV spectrophotometer.

Example 1

The preparation of the *Astragalus membranaceus* seed refined oil in the Example includes the following steps:

*Astragalus membranaceus* seeds were collected and impurities contained thereamong were picked out, then the *Astragalus membranaceus* seeds were washed clean and dried in air to produce dried *Astragalus membranaceus* seeds, which were then put into an oven for drying at 105° C. for 2 hours, then pulverized and ground to produce *Astragalus membranaceus* seeds powders with fineness of 40 meshes;

25 g of the *Astragalus membranaceus* seed powders was put into an extraction kettle of a supercritical fluid extraction system to perform static extraction for 1.5 hours at a $CO_2$ flow rate adjusted to a maximum level under a constant temperature of 50° C. and a constant pressure of 350 Pa, obtaining 1.0 g *Astragalus membranaceus* seed raw oil. Under this condition, the extraction yield of *Astragalus membranaceus* seed oil was up to about 4.0%, and the extraction rate reached about 60% calculated on the oil content of *Astragalus membranaceus* seeds, Refinement Steps Degumming treatment: the *Astragalus membranaceus* seed raw oil obtained above was heated to 50° C. while stirring, then hot water, in an amount of 4 wt % with respect to the weight of the raw oil and having a temperature similar to that of the raw oil, was poured evenly into the raw oil to form a first mixture, then the first mixture was stirred rapidly for 15 min and heated to 80° C., then stirring was stopped and the mixture was kept standing at 80° C. for 6 hours to obtain an upper layer comprising degummed oil and a lower layer comprising water and gums, then the lower layer was separated, obtaining the degummed oil in the upper layer;

Deacidification: 20 g of the degummed oil obtained above was put into a 150 mL conical flask, heated to 60° C. while shaking in a water bath shaker, then 100 mL of NaOH aqueous solution in a concentration of 7% by weight was added into the degummed oil to perform reaction for 30 min under stirring at 60° C. to form a second mixture, then the second mixture was centrifuged at 4000 r/min for 10 minutes, obtaining an upper layer of oil. In order to remove soap and free base remained therein, the upper layer of oil was collected and heated to 85° C., then the oil was washed twice with hot water and was centrifuged at 3000 r/min for 20 minutes, obtaining a deacidified oil in an upper layer;

Decoloration: 5 g of the deacidified oil was collected and put into 100 mL beaker, and was heated to 80° C. under shaking in a water bath shaker, then 0.20 g active white clay was added into the deacidified oil and mixed well to perform decoloration at 80° C. for 10 min, after which the deacidified oil was centrifuged at 4000 r/min for 10 minutes, obtaining a first decolored oil. In order to further decolor, the first decolored oil can be collected and mixed with a certain amount of active white clay to perform the above decoloration process again in the same manner, obtaining a second decolored oil, with a decoloration rate up to 96%.

Oil deodorization: the decolored oil above was collected and put into a round-bottom flask with double hole rubber plugs (a few glass beads were added to prevent bumping), and was heated using a electric jacket at a voltage controlled at 100-120 V, then stream was introduced through a glass tube and flowed upwards to perform stripping for 2 h such that uniform mass transfer occurs between the oil and the stream to produce a deodorized oil, thereafter the deodorized oil is dehydrated and dried by a rotary evaporator at a water bath temperature of 80° C. and a rotation speed of 120 r/min, until no water drops were distilled out, to produce a new refined oil.

Example 2

The preparation of the *Astragalus membranaceus* seed refined oil in the Example includes the following steps:

*Astragalus membranaceus* seeds were collected and impurities contained thereamong were picked out, then the *Astragalus membranaceus* seeds were washed clean and dried in air to produce dried *Astragalus membranaceus* seeds, which were then put into an oven for drying at 100° C. for 4 hours, then pulverized and ground to produce *Astragalus membranaceus* seeds powders;

25 g of the *Astragalus membranaceus* seed powders was put into an extraction kettle of a supercritical fluid extraction system to perform static extraction for 2.5 hours at a $CO_2$ flow rate adjusted to a maximum level under a constant temperature of 30° C. and a constant pressure of 350 Pa, obtaining 1.0 g *Astragalus membranaceus* seed raw oil. Under this condition, the extraction yield of *Astragalus membranaceus* seed oil was up to about 4.0%, and the extraction rate reached about 60% calculated on the oil content of *Astragalus membranaceus* seeds, Refinement Steps Degumming treatment: the *Astragalus membranaceus* seed raw oil obtained above was heated to 55° C. while stirring, then hot water, in an amount of 3 wt % with respect to the weight of the raw oil and having a temperature similar to that of the raw oil, was poured evenly into the raw oil to form a first mixture, then the first mixture was stirred rapidly for 15 min and heated to 85° C., then stirring was stopped and the mixture was kept standing at 85° C. for 6 hours to obtain an upper layer comprising degummed oil and a lower layer comprising water and gums, then the lower layer was separated, obtaining the degummed oil in the upper layer;

Deacidification: 20 g of the degummed oil obtained above was put into a 150 mL conical flask, heated to 50° C. while shaking in a water bath shaker, then 90 mL of NaOH aqueous solution in a concentration of 10% by weight was added into the degummed oil to perform reaction for 35 min under stirring at 50° C. to form a second mixture, then the second mixture was centrifuged at 4000 r/min for 10 minutes, obtaining an upper layer of oil. In order to remove soap and free base remained therein, the upper layer of oil was collected and heated to 70° C., then the oil was washed twice with hot water and was centrifuged at 3000 r/min for 20 minutes, obtaining a deacidified oil in an upper layer;

Decoloration: 5 g of the deacidified oil was collected and put into 100 mL beaker, and was heated to 90° C. under shaking in a water bath shaker, then 0.25 g active white clay was added into the deacidified oil and mixed well to perform decoloration at 90° C. for 15 min, after which the deacidified oil was centrifuged at 4000 r/min for 10 minutes, obtaining a first decolored oil. In order to further decolor, the first decolored oil can be collected and mixed with a certain amount of active white clay to perform the above decoloration process again in the same manner, obtaining a second decolored oil, with a decoloration rate up to 96%.

Oil deodorization: the decolored oil above was collected and put into a round-bottom flask with double hole rubber plugs (a few glass beads were added to prevent bumping), and was heated using a electric jacket at a voltage controlled at 100-120 V, then stream was introduced through a glass tube and flowed upwards to perform stripping for 2 h such that uniform mass transfer occurs between the oil and the stream to produce a deodorized oil, thereafter the deodorized oil is dehydrated and dried by a rotary evaporator at a water bath temperature of 70° C. and a rotation speed of 120 r/min, until no water drops were distilled out, to produce a new refined oil.

Example 3

The preparation of the *Astragalus membranaceus* seed refined oil in the Example includes the following steps:

*Astragalus membranaceus* seeds were collected and impurities contained thereamong were picked out, then the *Astragalus membranaceus* seeds were washed clean and dried in air to produce dried *Astragalus membranaceus* seeds, which were then put into an oven for drying at 105° C. for 2 hours, then pulverized and ground to produce *Astragalus membranaceus* seeds powders with fineness of 60 meshes;

25 g of the *Astragalus membranaceus* seed powders was put into an extraction kettle of a supercritical fluid extraction system to perform static extraction for 2.5 hours at a $CO_2$ flow rate adjusted to a maximum level under a constant temperature of 40° C. and a constant pressure of 250 Pa, obtaining 1.0 g *Astragalus membranaceus* seed raw oil. Under this condition, the extraction yield of *Astragalus membranaceus* seed oil was up to about 4.0%, and the extraction rate reached about 60% calculated on the oil content of *Astragalus membranaceus* seeds, Refinement Steps Degumming treatment: the *Astragalus membranaceus* seed raw oil obtained above was heated to 45° C. while stirring, then hot water, in an amount of 5 wt % with respect to the weight of the raw oil and having a temperature similar to that of the raw oil, was poured evenly into the raw oil to form a first mixture, then the first mixture was stirred rapidly for 15 min and heated to 75° C., then stirring was stopped and the mixture was kept standing at 75° C. for 6 hours to obtain an upper layer comprising degummed oil and a lower layer comprising water and gums, then the lower layer was separated, obtaining the degummed oil in the upper layer;

Deacidification: 20 g of the degummed oil obtained above was put into a 150 mL conical flask, heated to 70° C. while shaking in a water bath shaker, then 80 mL of NaOH aqueous solution in a concentration of 12% by weight was added into the degummed oil to perform reaction for 25 min under stirring at 70° C. to form a second mixture, then the second mixture was centrifuged at 4000 r/min for 10 minutes, obtaining an upper layer of oil. In order to remove soap and free base remained therein, the upper layer of oil was collected and heated to 90° C., then the oil was washed twice with hot water and was centrifuged at 3000 r/min for 20 minutes, obtaining a deacidified oil in an upper layer;

Decoloration: 5 g of the deacidified oil was collected and put into 100 mL beaker, and was heated to 70° C. under shaking in a water bath shaker, then 0.25 g active white clay was added into the deacidified oil and mixed well to perform decoloration at 70° C. for 25 min, after which the deacidified oil was centrifuged at 4000 r/min for 10 minutes, obtaining a first decolored oil. In order to further decolor, the first decolored oil can be collected and mixed with a certain amount of active white clay to perform the above decoloration process again in the same manner, obtaining a second decolored oil, with a decoloration rate up to 96%.

Oil deodorization: the decolored oil above was collected and put into a round-bottom flask with double hole rubber plugs (a few glass beads were added to prevent bumping), and was heated using a electric jacket at a voltage controlled at 100-120 V, then stream was introduced through a glass tube and flowed upwards to perform stripping for 2 h such that uniform mass transfer occurs between the oil and the stream to produce a deodorized oil, thereafter the deodorized oil is dehydrated and dried by a rotary evaporator at a water bath temperature of 90° C. and a rotation speed of 120 r/min, until no water drops were distilled out, to produce a new refined oil.

Example 4

*Astragalus membranaceus* seeds were collected and impurities contained thereamong were picked out, then the *Astragalus membranaceus* seeds were washed clean and dried in air to produce dried *Astragalus membranaceus* seeds, which were then put into an oven for drying at 105° C. for 2 hours, then pulverized and ground to produce *Astragalus membranaceus* seeds powders with fineness of 60 meshes;

25 g of the *Astragalus membranaceus* seed powders was put into an extraction kettle of a supercritical fluid extraction system to perform static extraction for 2.5 hours at a $CO_2$ flow rate adjusted to a maximum level under a constant temperature of 40° C. and a constant pressure of 250 Pa, obtaining 1.0 g *Astragalus membranaceus* seed raw oil. Under this condition, the extraction yield of *Astragalus membranaceus* seed oil was up to about 4.0%, and the extraction rate reached about 60% calculated on the oil content of *Astragalus membranaceus* seeds, Refinement Steps Degumming treatment: the *Astragalus membranaceus* seed raw oil obtained above was heated to 50° C. while stirring, then hot water, in an amount of 5 wt % with respect to the weight of the raw oil and having a temperature similar to that of the raw oil, was poured evenly into the raw oil to form a first mixture, then the first mixture was stirred rapidly for 15 min and heated to 80° C., then stirring was stopped and the mixture was kept standing at 80° C. for 6 hours to obtain an upper layer comprising degummed oil and a lower layer comprising water and gums, then the lower layer was separated, obtaining the degummed oil in the upper layer;

Deacidification: 20 g of the degummed oil obtained above was put into a 150 mL conical flask, heated to 60° C. while shaking in a water bath shaker, then 100 mL of NaOH aqueous solution in a concentration of 10% by weight was added into the degummed oil to perform reaction for 25 min under stirring at 60° C. to form a second mixture, then the second mixture was centrifuged at 4000 r/min for 10 minutes, obtaining an upper layer of oil. In order to remove soap and free base remained therein, the upper layer of oil was collected and heated to 80° C., then the oil was washed twice with hot water and was centrifuged at 3000 r/min for 20 minutes, obtaining a deacidified oil in an upper layer;

Decoloration: 5 g of the deacidified oil was collected and put into 100 mL beaker, and was heated to 70° C. under shaking in a water bath shaker, then 0.25 g active white clay was added into the deacidified oil and mixed well to perform decoloration at 70° C. for 25 min, after which the deacidified oil was centrifuged at 4000 r/min for 10 minutes, obtaining a first decolored oil. In order to further decolor, the first decolored oil can be collected and mixed with a certain amount of active white clay to perform the above decoloration process again in the same manner, obtaining a decolored refined oil.

Example 5

The *Astragalus membranaceus* seed refined oil obtained in Example 1 was prepared into soft capsules (500 mg/piece) according to the conventional technologies with conventional excipients. Administration of the prepared soft capsules twice (in morning and night) per person per day in an amount of 1.0-2.0 g each time for a period of 8-12 weeks, can effectively improve vascular function without any undesirable effects on the liver function, so the prepared soft capsules are considered to be a safe and effective health-care food with functions of lowering blood glucose, TC, TG and HDL-C.

Example 6

The *Astragalus membranaceus* seed refined oil obtained in Example 1 was prepared into tablets according to the conventional technologies with conventional excipients. The prepared tablets can be administrated regularly in a fixed amount, and are considered to be a safe and effective health-care food with functions of lowering blood glucose, TC, TG and HDL-C.

Example 7

The *Astragalus membranaceus* seed refined oil obtained in Example 1 was prepared into dripping pills according to the conventional technologies with conventional excipients. The prepared dripping pills can be taken regularly in a fixed amount, and are considered to be a safe and effective health-care food with functions of lowering blood glucose, TC, TG and HDL-C.

Example 8

The *Astragalus membranaceus* seed refined oil obtained in Example 1 was prepared into capsules according to the conventional technologies with conventional excipients, which can be taken regularly in a fixed amount and are considered to be a safe and effective health-care food with functions of lowering blood glucose, TC, TG and HDL-C.

Example 9

The *Astragalus membranaceus* seed refined oil obtained in Example 1 was prepared into granules according to the conventional technologies with conventional excipients, which can be taken regularly in a fixed amount and are considered to be a safe and effective health-care food with functions of lowering blood glucose, TC, TG and HDL-C.

Example 10

The *Astragalus membranaceus* seed refined oil obtained in Example 1 was prepared into mixtures according to the conventional technologies with conventional excipients, which can be taken regularly in a fixed amount and are considered to be a safe and effective health-care food with functions of lowering blood glucose, TC, TG and HDL-C.

Example 11

The *Astragalus membranaceus* seed refined oil obtained in Example 1 was prepared into pills according to the conventional technologies with conventional excipients, which can be taken regularly in a fixed amount and are considered to be a safe and effective health-care food with functions of lowering blood glucose, TC, TG and HDL-C.

Example 12

The *Astragalus membranaceus* seed refined oil obtained in Example 1 was blended with daily sesame oil in a weight ratio of 1:1 to obtain a blended oil that has a ratio of ω-6 to ω-3 in a range of 2-4:1, which is in accordance with the recommended standards adopted by The International Scientific Committee on Food, so the blended oil can be used as an oil product for daily cooking, cold vegetable dish in sauce, health-care and dining.

Example 13

The *Astragalus membranaceus* seed refined oil obtained in Example 1 was blended with daily walnut oil according to a weight ratio of 1:1 to obtain a blended oil that has a ratio of ω-6 to ω-3 in a range of 2-4:1, which is in accordance with the recommended standards adopted by The International Scientific Committee on Food, so the blended oil can be used as an oil product for daily cooking, cold vegetable dish in sauce, health-care and dining.

Example 14

The *Astragalus membranaceus* seed refined oil obtained in Example 1 was blended with daily peanut oil according to a weight ratio of 1:1 to obtain a blended oil that has an intake ratio of ω-6 to ω-3 in a range of 2-4:1, which is in accordance with the recommended standards adopted by The International Scientific Committee on Food, so the blended oil can be used as an oil product for daily cooking, cold vegetable dish in sauce, health-care and dining.

Obviously, the above examples are just for purpose of clear illustration and are not intended to limit the example mode. It will be obvious to those skilled in the art that changes and modifications may be made without departing from the invention in its broader aspects, and, therefore, the aim of the appended claims is to cover all such changes and modifications as fall within the true spirit and scope of the invention.

The invention claimed is:

1. A preparation for lowering blood glucose, hyperlipidemia, triglycerides and cholesterol comprising an effective amount of an *Astragalus membranaceus* seed raw oil and an excipient, wherein the preparation is in a dosage form selected from the group consisting of a tablet, dripping pill, capsule, and pill;

wherein the *Astragalus membranaceus* seed raw oil is obtained by extracting *Astragalus membranaceus* seeds with a supercritical carbon dioxide ($CO_2$) fluid; and wherein the extracting is carried out at a $CO_2$ flow rate adjusted to maximum, under a constant temperature of 30-50° C. and a constant pressure of 250-350 Pa, and lasts for 1.5-2.5 hours.

2. A preparation for lowering blood glucose, hyperlipidemia, triglycerides and cholesterol comprising an effective amount of an *Astragalus membranaceus* seed refined oil and an excipient, wherein the preparation is in a dosage form selected from the group consisting of a tablet, dripping pill, capsule, and pill;

wherein the *Astragalus membranaceus* seed refined oil is obtained by:
(a) extracting *Astragalus membranaceus* seeds with a supercritical carbon dioxide ($CO_2$) carried out at a $CO_2$ flow rate adjusted to maximum, under a constant temperature of 30-50° C. and a constant pressure of 250-350 Pa, and lasts for 1.5-2.5 hours, to obtain a *Astragalus membranaceus* seed raw oil,
(b) a degumming step: wherein the *Astragalus membranaceus* seed raw oil is heated to 45-55° C., then hot water, in an amount of 3-5 wt % with respect to the weight of the raw oil and having a temperature similar to that of the raw oil, is added and mixed well with the raw oil to form a first mixture, and the first mixture is heated to 75-85° C. under stirring, followed by standing and layering at 75-85° C., then a lower layer of water and gum is removed, and an upper layer of degummed oil is obtained;
(c) a deacidification step: wherein the degummed oil is collected and heated to 50-70° C. under shaking, then NaOH aqueous solution in a concentration of 7-12% by weight is added into the degummed oil at 50-70° C. to form a second mixture, the second mixture is centrifuged and an upper layer of oil is collected and heated to 70-90° C., then the oil is washed with hot water and is centrifuged, obtaining a deacidified oil in an upper layer; and
(d) a decoloration step: wherein the deacidified oil is collected and heated to 70-90° C., then an active white clay in an amount of 4-6 wt % with respect to the weight of the deacidified oil is added into the deacidified oil for performing decoloration at 70-90° C. for at least once, after which the deacidified oil is centrifuged, obtaining a refined oil in an upper layer.

* * * * *